United States Patent [19]

Addiss

[11] Patent Number: 5,623,938

[45] Date of Patent: Apr. 29, 1997

[54] METHOD AND APPARATUS FOR RESPIRATION MONITORING

[75] Inventor: Robert R. Addiss, Westford, Mass.

[73] Assignee: Siemens Medical Systems, Inc., Iselin, N.J.

[21] Appl. No.: 537,175

[22] Filed: Sep. 29, 1995

[51] Int. Cl.$^6$ ....................................... A61B 5/08
[52] U.S. Cl. .................. 128/723; 128/716; 128/204.18; 128/204.21; 128/204.23
[58] Field of Search ..................... 128/716, 721, 128/723, 671, 204.18, 204.21, 204.23

[56] References Cited

U.S. PATENT DOCUMENTS

| | | | |
|---|---|---|---|
| 3,452,743 | 7/1969 | Rieke | 128/723 |
| 3,524,058 | 8/1970 | Robertson et al. | 128/723 |
| 4,506,678 | 3/1985 | Russell et al. | 128/723 |
| 4,708,146 | 11/1987 | Lane | 128/723 |
| 4,823,797 | 4/1989 | Heinze et al. | 128/723 |
| 4,919,145 | 4/1990 | Marriott | 128/723 |
| 5,335,669 | 8/1994 | Bowman et al. | 128/723 |
| 5,469,859 | 11/1995 | Tsoglin et al. | 128/723 |

OTHER PUBLICATIONS

Hewlett–Packard Clover Monitor (Model 78534) Operation Manual, pp. 2–13 and FIG. 5–19.

*Primary Examiner*—Vincent Millin
*Assistant Examiner*—William J. Deane, Jr.
*Attorney, Agent, or Firm*—Lawrence C. Edelman

[57] ABSTRACT

An apparatus for monitoring the expansion and contraction of the thoracic cavity of a patient caused by respirations comprises, generating means for generating an AC examination current signal, coupling means for applying the examination current signal to the patient so that the examination current passes through the thoracic cavity of the patient, but at least a portion of the current does not pass through the thoracic cavity of the patient, detecting means coupled to the coupling means for detecting an amplitude modulated voltage signal developed across the patient in response to the application of the examination current and variation of the transthoracic impedance of the patient due to respiration, and current modifying means coupled with the generating means for modifying the AC examination current during application to the patient so that the portion of the examination current which does not pass through the patient is at least partially compensated.

14 Claims, 3 Drawing Sheets

METHOD AND APPARATUS FOR RESPIRATION MONITORING

BACKGROUND OF THE INVENTION

1. Field of the Invention

The present invention relates to monitoring respirations of a patient, and more specifically to impedance pneumography, which is a technique for monitoring respirations by monitoring changes in electrical impedance caused by the expansion and contraction of the thoracic cavity of the patient during respiration.

2. Description of the Prior Art

Typically, a differential, constant amplitude AC examination current is applied to the body of a patient for detecting patient respirations by measuring changes in the transthoracic impedance of the patient. The examination current is applied to the patient by two of the electrodes normally used for ECG monitoring. The examination current is passed through the thoracic cavity of the patient and, due to the constant amplitude examination current passing through a transthoracic impedance that changes with patient respirations, voltage modulations are created at the ECG electrodes in accordance with the patient respirations. The resulting voltage modulations are typically detected by a synchronous voltage detector, connected to the same pair of electrodes as was used for applying the examination current, such as the right arm (RA) and left arm (LA) electrodes.

The cables used for connecting the examination current and voltage detector to the patient contain capacitive reactances which tends to shunt a portion of the examination current around the patient. One effect of this shunting is that the system gain, as expressed in Volts/Ohm, will have a dependency on the baseline level of the transthoracic impedance, as well as the level of any impedance placed in series with the patient, such as resistances for protecting the monitoring circuitry from defibrillator voltages which may be applied to the patient. This dependency makes detecting the small respiration induced changes in impedance more difficult (that is, such a dependency making it difficult to set absolute signal detection threshold levels). Another effect is that the induced voltage becomes sensitive to changes in the frequency of the examination current. Any phase or frequency jitter in the examination current signals, or the clock signals used to detect the examination current, will be converted to a voltage noise during detection by the synchronous voltage detector. The above-noted shunting of the examination current, changes in the system gain, and voltage noise result in signal artifacts in the induced voltage modulations which reduce the accuracy of the respiration detection circuitry.

It is an object of the present invention to provide an AC examination current source which will solve these undesirable effects, while providing a current source which is relatively low in cost, which will present minimum load to ECG signals acquired by the electrodes, and able to be easily manufactured using integrated circuit technology.

A prior art respiration monitor manufactured by Hewlett-Packard (believed to be sold under the trademark CLOVER) applies a fixed frequency sine wave to an impedance bridge, one leg of which is connected to the thoracic cavity of a patient via a transformer. It is believed that the magnetizing inductance of the transformer may be intended to at least partially compensate for the capacitance in the patient cable although this is not specifically known. The output of the bridge is fed to a synchronous detector for developing the respiration signal in accordance with known techniques. Although the transformer in this monitor may provide some compensation for the capacitance of the patient cable, the technique undesirably requires the use of a transformer, which is bulky and not well suited for incorporation with integrated circuit technology. Additionally, this technique requires a sinewave examination current, which is somewhat difficult and costly to generate using digital circuitry.

SUMMARY OF THE INVENTION

An apparatus for monitoring the expansion and contraction of the thoracic cavity of a patient caused by respirations comprises, generating means for generating an AC examination current signal, coupling means for applying the examination current signal to the patient so that the examination current passes through the thoracic cavity of the patient, but at least a portion of the current does not pass through the thoracic cavity of the patient, detecting means coupled to the coupling means for detecting an amplitude modulated voltage signal developed across the patient in response to the application of the examination current and variation of the transthoracic impedance of the patient due to respiration, and current modifying means coupled with the generating means for modifying the AC examination current during application to the patient so that the portion of the examination current which does not pass through the patient is at least partially compensated.

DETAILED DESCRIPTION OF THE INVENTION

Figure 1:
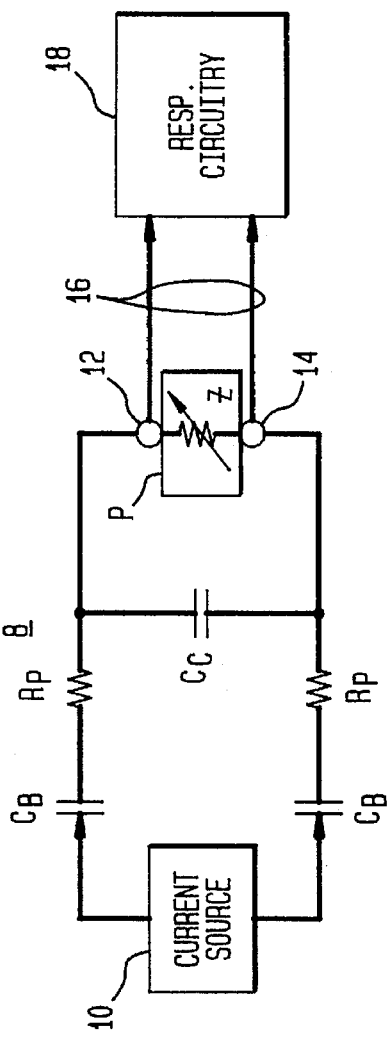
FIG. 1 illustrates in block diagram form a prior art respiration monitor.

FIG. 1 illustrates a prior art respiration monitor 8 wherein a differential current source 10 generates two identical, but differential (180° out of phase), AC examination currents. The differential currents are applied to patient mounted electrodes 12 and 14, respectively, via a patient connected cable 16. Typically, the electrodes are of the type used for EKG monitoring, and patient cable 16 is the EKG cable used to connect the EKG electrodes to an EKG monitor. In this case, EKG signal processing circuitry (not shown) would also be connected to cable 16 in parallel with respiration circuitry 18, for developing and displaying EKG waveforms, as well known. As also well known, the body of a patient P presents a varying impedance Z between electrodes 12 and 14, the variations in the patient impedance corresponding to the expansion and contraction of the transthoracic cavity of the patient in response to patient respirations. Respiration circuitry 18 within the monitor is connected to the electrodes 12 and 14 via cable 16 for sensing amplitude modulations of a voltage developed between electrodes 12 and 14 due to the applied AC examination current and the patient respirations. In a manner well known to those of ordinary skill in the art, these sensed amplitude modulations are processed for developing a respiration signal which may be used for display and/or alarm monitoring of the respirations of the patient. Also illustrated are $C_C$, the effective capacitance of cable 16, and $C_B$ and $R_P$, comprising a DC blocking capacitor and a high voltage protection resistor, respectively.

The effective capacitance $C_C$ of cable 16 tends to shunt a portion of the AC examination current around, rather than through, the patient. One major effect of this shunting is a reduced signal level of the induced voltage modulations, thereby reducing the ability to accurately monitor the changes in patient impedance, which is on the order of only 1 or 2 Ohms out of approximately 600 to 6000 Ohms of patient impedance. At approximately 5000–6000 Ohms of patient impedance, current shunting by the cable is significant. Other undesirable and related effects of the cable capacitance $C_C$ are the variation and gain, as expressed in Volts/Ohm, and the conversion into voltage variations by the synchronous detector of frequency and/or phase jitter in the examination current, as previously noted in the Background portion of this specification.

Figure 2:
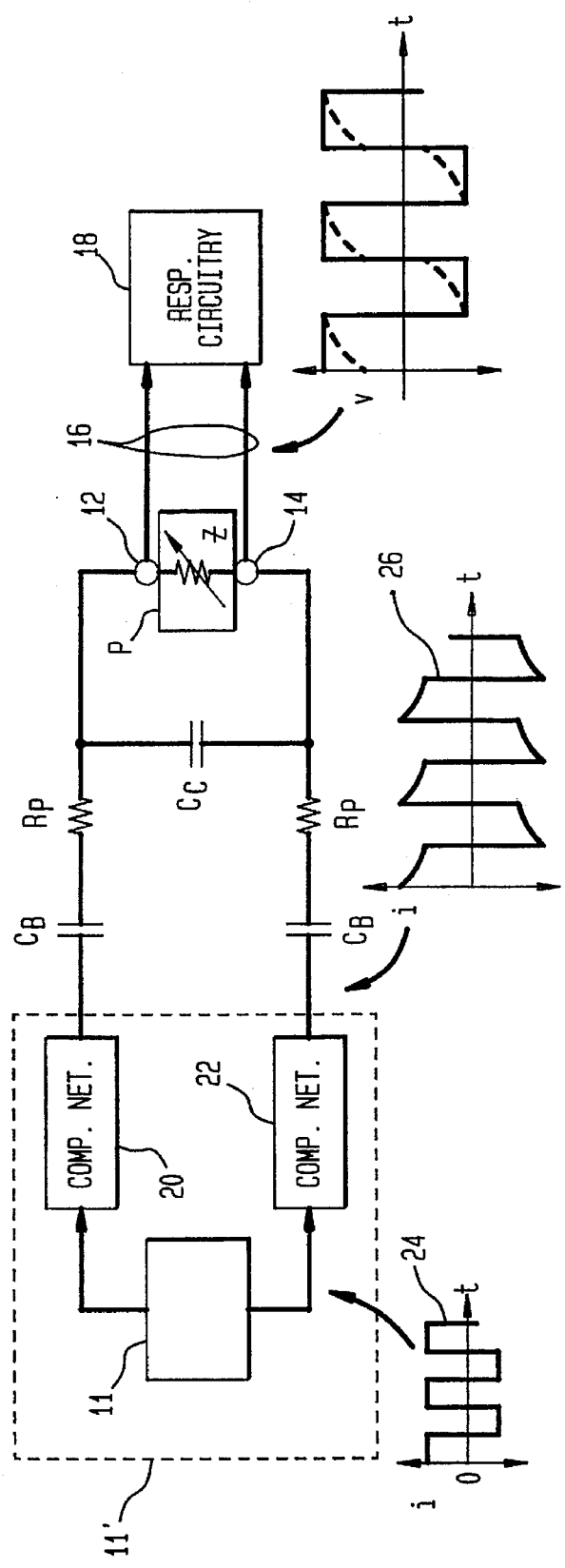
FIG. 2 illustrates in block diagram form a respiration monitor constructed in accordance with the principles of the present invention.

In FIG. 2, a block diagram of a respiration monitor constructed in accordance with the principles of the present invention is shown. Circuits and components that are substantially the same in FIGS. 1 and 2 are similarly numbered. Basically, there are at least two improvements over the prior art. Firstly, compensation networks 20 and 22 are incorporated with the differential outputs of current source 10 forming a modified current source 10' and secondly, in the preferred embodiment, the differential current source is provided using a switched "flying" capacitor circuit arrangement.

As shown in FIG. 2, a differential current source 11 provides a square wave examination current 24 (of, for example, ±100 µA), and compensation networks 20 and 22 modify the examination current so as to develop a compensated current at the respective outputs of current source 11' which has an overshoot at its leading edges, as illustrated by waveform 26. Waveform 28 is illustrative of the voltage developed across the patient in response to application to the patient of the compensated examination current, which voltage is transmitted to the respiration detection circuits 18 via cable 16. Note that the level transitions in waveform 28 are substantially rectangular, wherein if the compensated examination current, as illustrate by waveform 26, were not provided, a portion of the examination current will initially be shunted across the patient by the capacitance $C_c$ of cable 16, and then slowly increase thereafter. This undesired effect of the cable capacitance, if left uncompensated, would result in a voltage waveform 28 having degraded leading edges at the signal level transitions, such as shown by the curved dashed-line portions in waveform 28. These curved portions indicate a reduced amplitude level voltage signal (i.e., one with a reduced S/N) into the respiration detector (as well as an unwanted amplitude level variation), which, as previously noted, can result in monitoring inaccuracies when developing the respiration signal. Compensation networks 20 and 22 develop the compensated examination current so that the combined effect of the overshoot in the examination current with the shunting effect of cable capacitor $C_c$ is a substantially square wave voltage waveform 28 at the input to respiration circuitry 18.

Figure 3:
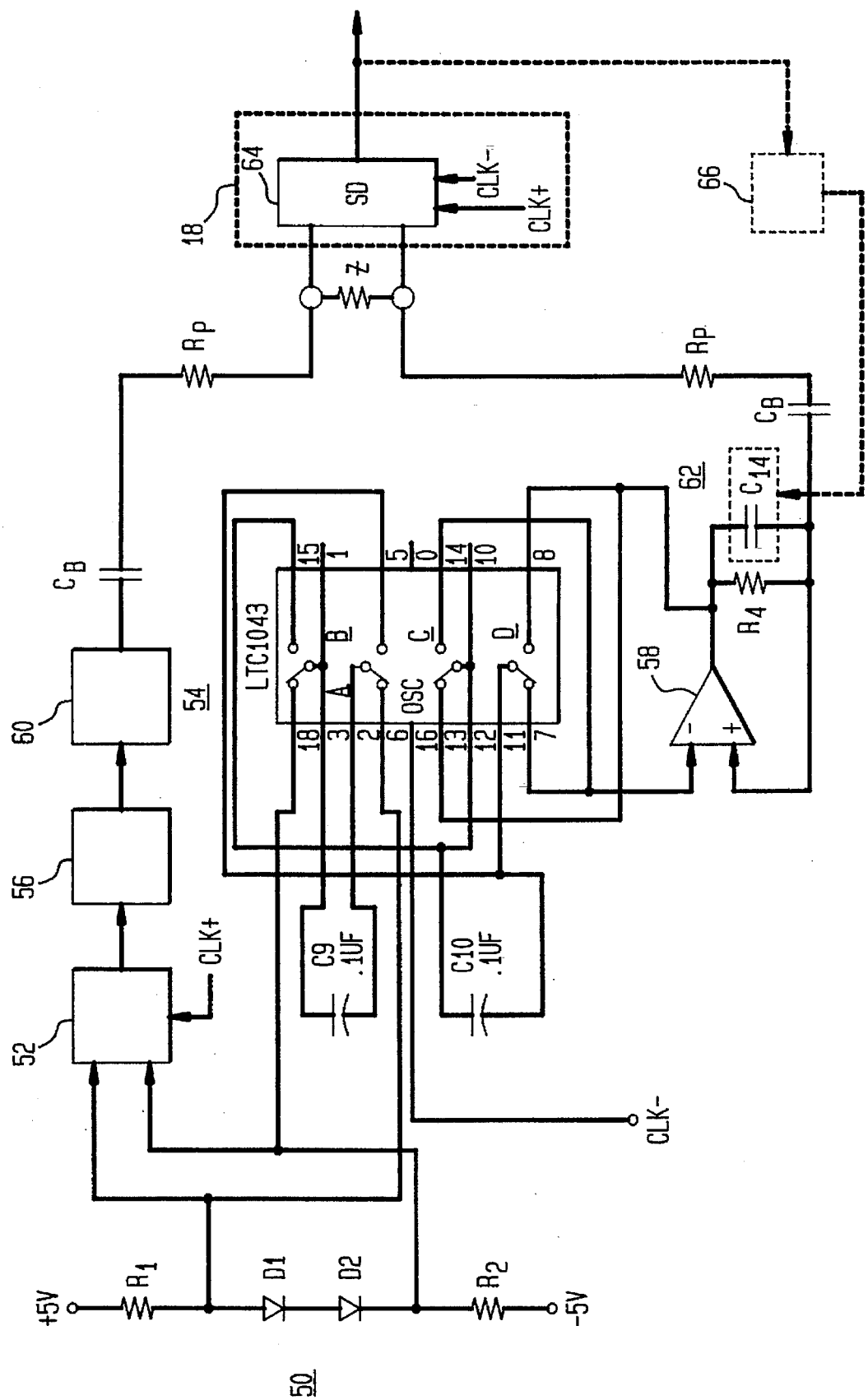
FIG. 3 illustrates partially in block diagram form and partially in schematic diagram form the respiration monitor shown in FIG. 2.
Figure 4:
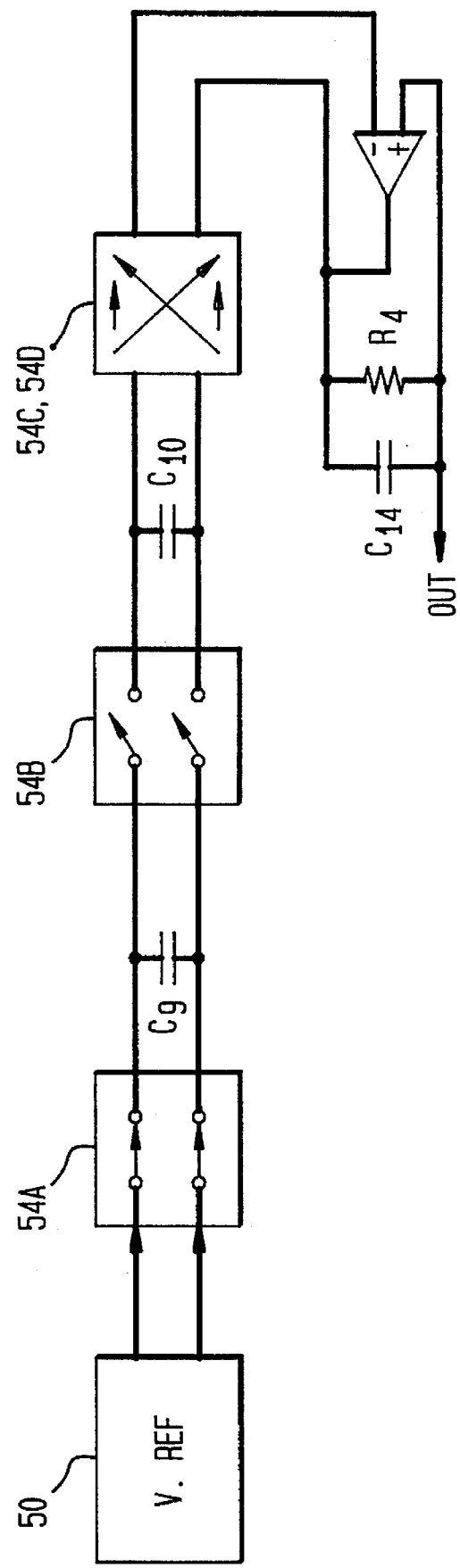
FIG. 4 illustrates in block diagram form the functional operation of a portion of the schematic shown in FIG. 3.

FIG. 3 illustrates partially in block diagram form and partially in detailed schematic diagram form a respiration monitor constructed in accordance with the principles of the present invention, including the compensated current source 11'. Note, since the compensated current source 11' develops two identical differential AC currents that are 180° out of phase, and basically comprises two identical current sources, details of only one-half of the circuitry will be described. In this regard, in conjunction with this description, reference should also be made to the functional block diagram shown in FIG. 4, which functionally describes the operation of one-half of the switching arrangement forming current source 11. A voltage reference 50 comprises series connected diodes $D_1$ and $D_2$, which are forward biased via resistors $R_1$ and $R_2$ connected to power supply voltages of +5 volts and −5 volts, respectively. First and second substantially identical switching arrangements 52 and 54 are simultaneously coupled to the positive and negative sides, respectively, of voltage reference source 50 for developing in a complimentary manner first and second differential voltage signals, respectively. A system clock (not shown) provides complimentary (180° out of phase) clock signals $CLK^+$ and $CLK^-$, which are provided to switching arrangements 52 and 54, respectively. The first and second differential voltage signals provided by switching arrangements 52 and 54 are then converted to current signals via first and second voltage to current (V/I) converters 56 and 58, respectively.

In accordance with the principles of the invention, the examination current signals developed at the output of converters 56 and 58 are modified by compensation networks 60 and 62, respectively, before being applied to the patient via the previously described blocking capacitor, high voltage protection resistor, patient cable and patient electrodes. The modification is by an amount sufficient to substantially compensate for the undesirable shunting of the examination current around the patient.

Referring again to FIGS. 3 and 4, voltage reference 50 provides a low impedance reference source for charging a "flying" capacitor $C_9$ via a clocked integrated circuit switch arrangement 54, which includes switch portions 54A that are normally closed in response to the $CLK^-$ clock signals, as shown. On the first half-cycle of the $CLK^-$ clock signal, switch portion 54A connects capacitor $C_9$ across reference voltage source 50. On the second half-cycle of $CLK^-$ clock signal, switch portion 54B connects capacitor $C_9$ across capacitor $C_{10}$, thereby maintaining a steady state voltage on capacitor $C_{10}$ at a value equal to the reference voltage. A reversing switch arrangement comprising switches 54C and 54D alternately reverses the polarity of the voltage developed across capacitor $C_{10}$ for application to a voltage to current (V/I) converter amplifier 58. Amplifier 58 forces the voltage on capacitor $C_{10}$ to appear across compensation network 62. The timing of switches 54C and 54D are controlled by the $CLK^-$ clock signal, with normal switch positions as shown in FIG. 3. The output of amplifier 58 is provided as the examination current after being modified via compensation network 62. Network 62 comprises a parallel connection of $R_4$ and $C_{14}$.

Compensation of the current source is achieved as follows. At the instant the voltage across the compensation network 62 changes polarity, due to the operation of reversing switch 54C/54D, a transient current substantially larger than the steady state current is created by a rapid charging action of capacitor $C_{14}$ by amplifier 58. This transient current is used to rapidly charge the distributed capacitance in patient cable 16. This transient current surge then decays at an exponential rate, as determined by the RC time constant of $R_4$ and $C_{14}$ of compensation network 62. If the product of $R_4$ and $C_{14}$ is made to be substantially equal to the RC product formed by the transthoracic impedance of the patient and the distributed capacitance of the patient cable, then the effects of cable capacitance can be substantially diminished. The extra current provided by current source 11' compensates for the amount of examination current that shunts around the patient due to cable capacitance $C_C$, rather than flowing through his transthoracic cavity. This will maximize the S/N of the developed voltage modulation signal applied to the synchronous detector 64 at the input of respiration detection circuitry 18. Synchronous detector 64 operates in a manner well known to those of ordinary skill in the art, and is responsive to the CLK$^+$ and CLK$^-$ clock signals for detecting the AC voltage, with amplitude modulations corresponding to respirations, generated at its output.

The setting of $R_4$ and $C_{14}$ can be made at the factory during manufacture, using fixed valves that provide appropriate compensation for typical patients, as determined by trial and error during circuit design. Alternatively, the output of the synchronous detector portion of respiration circuit 18 could be monitored for a predetermined output level while $C_{14}$ is manually adjusted by the user.

Thus, there has been shown and described a novel method and apparatus which satisfies all the objects and advantages sought therefore. Many changes, modifications, variations and other uses and applications of the subject invention will, however, become apparent to those skilled in the art after considering this specification and its accompanying drawings, which disclose preferred embodiments thereof. For example, the above-noted adjustment of capacitor $C_{14}$ can be made automatic by using a varactor diode as $C_{14}$ and developing a control signal from the output of the synchronous detector which is applied in a feedback manner to diode $C_{14}$. Furthermore, although current source 11 is illustrated using a switched capacitor arrangement, other arrangements for generating a current source are also possible, such as a large valve resistor, but which are not as advantageous as the illustrated embodiment. All such changes, modifications, variations and other uses and applications which do not depart from the spirit and scope of the invention are deemed to be covered by the invention which is limited only by the claims which follow.

I claim:

1. An apparatus for monitoring the expansion and contraction of the thoracic cavity of a patient caused by respiration, comprising:

generating means for generating an AC examination current signal;

coupling means for applying said examination current signal to the patient so that said examination current passes through said thoracic cavity of the patient, but at least a portion of said current does not pass through said thoracic cavity of the patient;

detecting means coupled to said coupling means for detecting an amplitude modulated voltage signal developed across said patient in response to said application of the examination current and variation of the transthoracic impedance of the patient due to respiration; and current modifying means coupled with the generating means for modifying the AC examination current during application to the patient so that said portion of the examination current which does not pass through said patient is at least partially compensated.

2. Apparatus in accordance with claim 1, wherein said modifying means applies an additional amount of current to said examination current which is substantially equal to said portion of said examination current which does not pass through said patient.

3. Apparatus in accordance with claim 2, wherein said portion of said examination current which does not pass through said patient is a time varying portion, and said modifying means provides a time varying change to the level of said examination current in a manner so as to compensate for said portion of said examination current which does not pass through said patient.

4. Apparatus in accordance with claim 1, wherein said modifying means comprises a parallel connection of a resistance and a capacitance, which is coupled to said coupling means, and wherein the RC time constant of said modifying means is substantially equal to an RC time constant of said coupling means.

5. Apparatus in accordance with claim 1, wherein said coupling means comprises a cable connected at one end to said patient and at another end to said apparatus for monitoring.

6. Apparatus in accordance with claim 1, wherein said generating means comprises:

a voltage reference source for providing first and second opposite polarity voltages;

a first switching arrangement for periodically coupling said first and second reference voltages to opposite sides of a first capacitance;

a second switching means for alternately coupling during time periods which are 180° out of phase with the periodic coupling of said reference voltage source to said first capacitance, said first capacitance to a second capacitance;

a reversing switch means for providing at its output during alternate time periods a voltage developed across said second capacitance and an inverse polarity of said voltage developed across said second capacitance; and a voltage to current converter having an input responsive to the output of said switching means for providing at an output an AC examination current.

7. Apparatus in accordance with claim 6, wherein said voltage to current converter comprises an operational amplifier.

8. Apparatus in accordance with claim 7, wherein said modifying means comprises a parallel connection of a resistor and capacitor coupled between an output of said operational amplifier means and its input.

9. Apparatus in accordance with claim 1, wherein said detecting means comprises a synchronous detector having an input coupled to said coupling means.

10. Apparatus in accordance with claim 1, further including adjustment means coupled to said current modifying means for adjusting the amount of compensation provided thereby.

11. Apparatus in accordance with claim 10, wherein said adjusting means comprises a feedback means connected between an output of said synchronous detector and said current modifying means for automatically adjusting said compensation.

12. A method for monitoring the expansion and contraction of the thoracic cavity of a patient caused by respiration, comprising:

generating an AC examination current signal;

applying said examination current signal to the patient so that said examination current passes through said thoracic cavity of the patient, but wherein at least a portion of said current does not pass through said thoracic cavity of the patient;

detecting an amplitude modulated voltage signal developed across said patient in response to said application of the examination current and variation of the transthoracic impedance of the patient due to respiration; and modifying the AC examination current during application to the patient so that said portion of the examination current which does not pass through said patient is at least partially compensated.

13. The method of claim 12, wherein said modifying step comprises applying an additional amount of current to said examination current which is substantially equal to said portion of said examination current which does not pass through said patient.

14. The method of claim 13, wherein said portion of said examination current which does not pass through said patient is a time varying portion, and said modifying step provides a time varying change to the level of said examination current in a manner so as to compensate for said portion of said examination current which does not pass through said patient.

* * * * *